United States Patent
Rothschild

(10) Patent No.: US 7,551,714 B2
(45) Date of Patent: Jun. 23, 2009

(54) COMBINED X-RAY CT/NEUTRON MATERIAL IDENTIFICATION SYSTEM

(75) Inventor: Peter J. Rothschild, Boston, MA (US)

(73) Assignee: American Science and Engineering, Inc., Billerica, MA (US)

( * ) Notice: Subject to any disclaimer, the term of this patent is extended or adjusted under 35 U.S.C. 154(b) by 41 days.

(21) Appl. No.: 11/741,191

(22) Filed: Apr. 27, 2007

(65) Prior Publication Data

US 2007/0286339 A1 Dec. 13, 2007

Related U.S. Application Data

(60) Provisional application No. 60/798,159, filed on May 5, 2006.

(51) Int. Cl.
  *G01N 23/222* (2006.01)
  *G01N 23/05* (2006.01)
  *G01N 23/083* (2006.01)
  *G01N 23/09* (2006.01)
  *G01N 23/10* (2006.01)
  *H05G 1/60* (2006.01)

(52) U.S. Cl. ............... 378/46; 378/44; 378/45; 378/57

(58) Field of Classification Search ........ 378/44, 378/45, 46, 57
  See application file for complete search history.

(56) References Cited

U.S. PATENT DOCUMENTS

| | | | | |
|---|---|---|---|---|
| 3,832,545 A | * | 8/1974 | Bartko | 376/159 |
| 5,124,554 A | * | 6/1992 | Fowler et al. | 250/358.1 |
| 5,479,023 A | * | 12/1995 | Bartle | 250/390.04 |
| 5,606,167 A | * | 2/1997 | Miller | 250/390.04 |
| 5,712,926 A | * | 1/1998 | Eberhard et al. | 382/205 |
| 5,838,759 A | | 11/1998 | Armistead | |
| 6,553,094 B1 | * | 4/2003 | Bernardi et al. | 378/57 |
| 7,023,956 B2 | * | 4/2006 | Heaton et al. | 378/57 |
| 7,254,211 B2 | * | 8/2007 | Hunt et al. | 378/20 |

(Continued)

FOREIGN PATENT DOCUMENTS

WO   WO 96/13839   5/1996

(Continued)

OTHER PUBLICATIONS

Rynes et al., "Gamma-ray and neutron radiography as part of a pulsed fast neutron analysis inspection system", Nucl. Instr. And Meth in Phys. Res., A422, pp. 895-899, 1999.

(Continued)

*Primary Examiner*—Allen C. Ho
(74) *Attorney, Agent, or Firm*—Bromberg & Sunstein LLP

(57) ABSTRACT

A system and methods for identifying contents of an enclosure such as an air cargo container. A three-dimensional image indicative of at least one of the CT number and the density of contents of the enclosure is obtained using penetrating radiation such as x-rays. If one or more suspect regions are identified among contents of the enclosure, a collimated neutron beam is activated to traverse each suspect region and fluorescent emission from the suspect region is detected, allowing material within the suspect region to be characterized based at least on the detected fluorescent emission. Additionally, the collimated neutron beam may be employed for neutron imaging of the contents of the enclosure.

20 Claims, 2 Drawing Sheets

U.S. PATENT DOCUMENTS

| | | |
|---|---|---|
| 7,356,115 B2 | 4/2008 | Ford et al. |
| 7,359,480 B2 * | 4/2008 | Slaughter et al. ............. 378/57 |
| 7,379,530 B2 * | 5/2008 | Hoff et al. ..................... 378/57 |
| 7,399,976 B2 * | 7/2008 | Kang et al. ............ 250/390.04 |
| 2003/0147484 A1 | 8/2003 | Olshansky et al. |

FOREIGN PATENT DOCUMENTS

| | | |
|---|---|---|
| WO | WO 2004/053472 | 6/2004 |

OTHER PUBLICATIONS

International Searching Authority, Notification of Transmittal of the International Search Report and Written Opinion of the International Searching Authority, PCT/US2007/067607, dated Jan. 22, 2008, 13 pages.

* cited by examiner

COMBINED X-RAY CT/NEUTRON MATERIAL IDENTIFICATION SYSTEM

The present application claims the priority of U.S. Provisional Patent Application Ser. No. 60/798,159, which was filed May 5, 2006, and which is incorporated herein by reference.

TECHNICAL FIELD

The present invention relates to methods and systems for the use of x-ray computer tomography in combination with neutron-activated gamma ray spectroscopy for inspection of materials.

BACKGROUND OF THE INVENTION

X-ray Computerized Tomography (CT) is currently the only automated explosive detection technique for the aviation industry that has been certified by the United States Government. The technique involves taking x-ray images at many different angles through an object and using mathematical reconstruction algorithms (such as filtered back-projection) to reconstruct tomographic slices through the object. These slices can then be combined to form a three-dimensional model of the object. In particular, the method allows the density of organic materials concealed inside the container to be determined, along with their size, volume, shape, and mass. This information can then be used to automatically detect explosives by looking for objects above a minimum size and mass, which have a density in the range of about 1.1-1.8 grams per cubic centimeter.

When used to screen checked baggage at airports, the typical false alarm rate for X-ray CT systems is between about 20% and 35%. It is therefore quite likely that for a typical air cargo container, several items in the container will have a density that lies in the density range of explosives, and false alarms would thus overwhelm airport cargo flow.

SUMMARY OF THE INVENTION

In accordance with preferred embodiments of the present invention, methods and apparatus are provided for using an X-Ray CT system that measures density as a level one system, in combination with a level two system that uses energetic neutrons to perform specific material identification.

As used herein, the term "CT number" refers to the attenuation of penetrating radiation per unit distance within an object material.

In accordance with one method provided by the invention, steps are provided of:

a. obtaining a three-dimensional image indicative of at least one of CT number and density of contents of the enclosure;

b. identifying a suspect region of contents of the enclosure based on at least one of CT number and density;

c. activating a collimated neutron beam to traverse a suspect region;

d. detecting fluorescent emission from the suspect region; and e. characterizing material within the suspect region based at least on the detected fluorescent emission.

In accordance with various embodiments of the invention, the step of obtaining a three-dimensional image may include scanning the enclosure with penetrating radiation, and, additionally, detecting penetrating radiation after traversal of the enclosure. Scanning the enclosure may include rotating or translating the enclosure, or doing the same with a source of penetrating radiation. Similarly, the enclosure or the source may be elevated during the course of scanning the enclosure.

In other embodiments of the invention, neutrons from the neutron beam that have traversed the enclosure may be detected. Detecting fluorescent emission from the suspect region may include energy resolution of the fluorescence.

In accordance with another aspect of the invention, a system is provided for identifying threat materials within an enclosure. The system has a CT scanner for obtaining a three-dimensional image indicative of at least one of CT number and density of contents of the enclosure and a processor for identifying a suspect region of contents of the enclosure based on at least one of CT number and density. Additionally, the system has a source for generating a collimated neutron beam to traverse the suspect region and a detector for detecting fluorescent emission from the suspect region, as well as a second processor for characterizing material within the suspect region based at least on the detected fluorescent emission, where the first and second processors, in certain embodiments, are embodied in a single processor.

BRIEF DESCRIPTION OF THE DRAWINGS

The foregoing features of the invention will be more readily understood by reference to the following detailed description taken with the accompanying drawings.

DETAILED DESCRIPTION OF PREFERRED EMBODIMENTS

In accordance with preferred embodiments of the present invention, a method is provided for using an X-Ray CT system as the level one system, combined with a level two system that uses energetic neutrons to perform specific material identification. Even if the false alarm rate of the x-ray CT system (the "level one" system) approaches unity, if the x-ray CT system is followed with a second "level two" system which is able to resolve these false alarms, then the false alarm rate of the combined system may be reduced to the false alarm rate of the level two system. By using a level two system which is able to identify the actual elemental makeup of the suspect material identified by the level one system, very low false alarm rates can be achieved, while not compromising the detection rate of the combined system.

The x-ray CT system may measure density of materials, with density serving as a criterion for identifying potential threat materials to be subjected to the next level of scrutiny.

Figure 1:
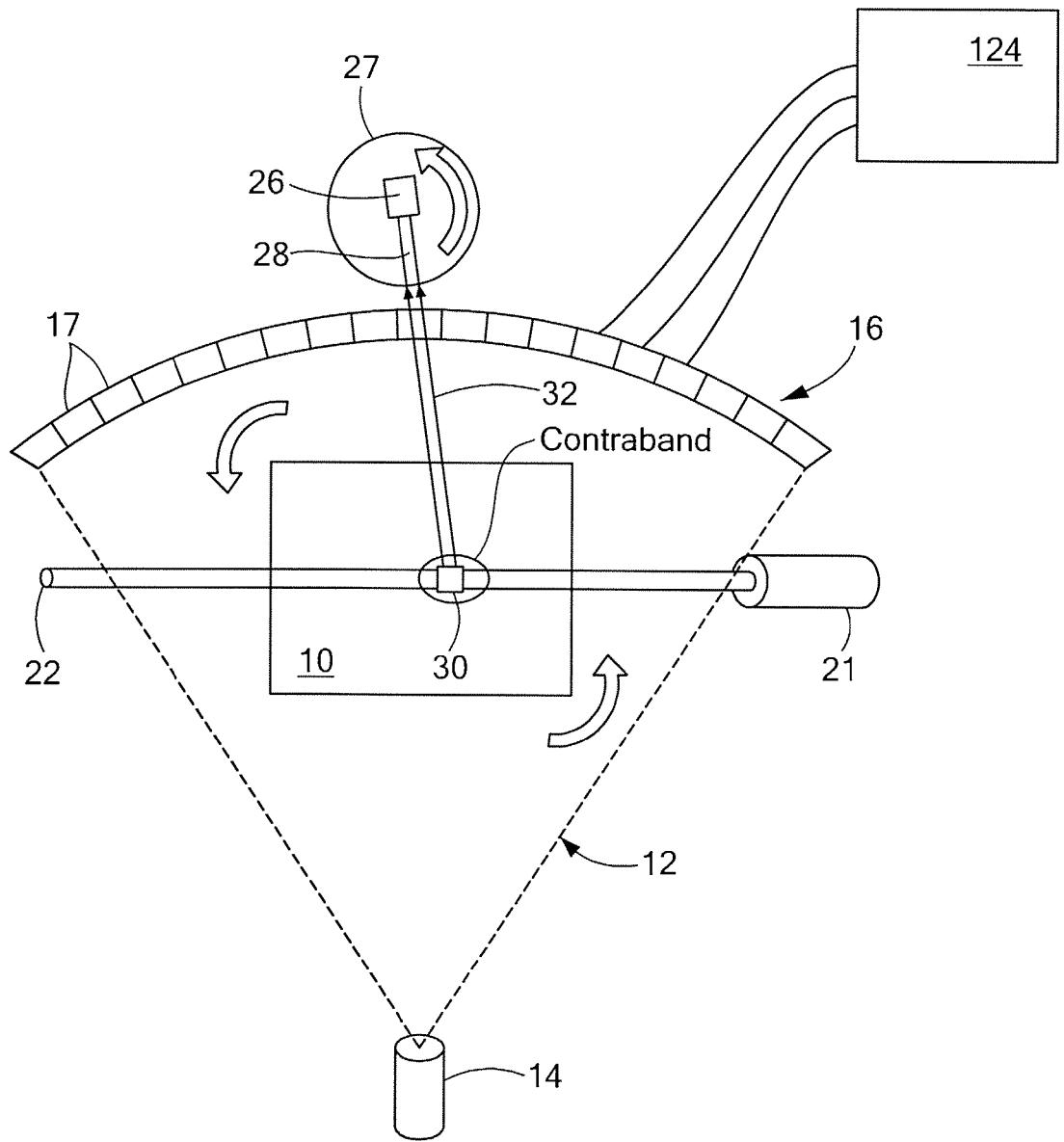
FIG. 1 is a schematic plan view of a combined x-ray/neutron inspection system in accordance with preferred embodiments of the present invention.
Figure 2:
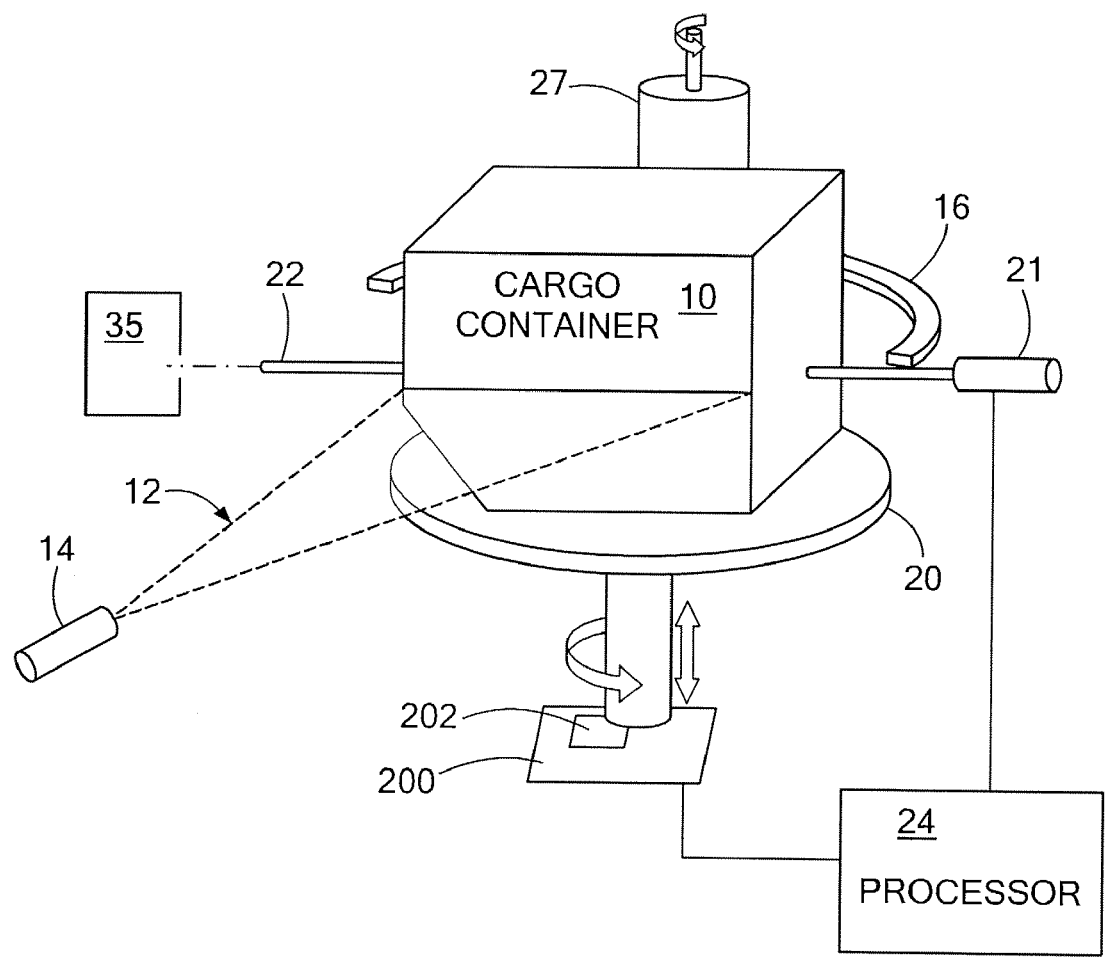
FIG. 2 shows a schematic isometric view of the components of the embodiment of the invention depicted in FIG. 1.

The combined X-Ray CT/Neutron system is shown in both FIGS. 1 and 2. An object 10 to be inspected (such as an LD3 air cargo container, for example) is placed on a rotating platform 20, which can also be raised and lowered by means of actuator 200, which may also contain one or more sensors 202 for sensing the position or orientation of the enclosure. In the present description, the invention may be described in terms of an air cargo container, however it is to be understood that such description is without limiting intent, and that any object of inspection is within the scope of the present invention and of any appended claims.

A horizontal fan beam 12 of penetrating radiation is incident on the container 10. The penetrating radiation may be x-rays, or may be other penetrating radiation, such as gamma rays, but will be referred to herein, for convenience, and without loss of generality, as x-rays. The penetrating radiation may be generated by an x-ray tube 14, for example, or by another type of source, all provided as examples, and without limitation.

Penetrating radiation that is transmitted through the container 10 is detected by an array 16 of segmented detectors 17 on the distal side of container 10. The detector array 16 can be linear or the detector elements can be positioned on an arc around the container, as shown in both FIGS. 1 and 2, or in other configurations.

An essentially horizontal collimated beam 22 of high-energy neutrons is produced by a neutron generator 21 which can be turned on or off by a system processor 24. In certain embodiments of the invention, neutron generator 21 may include a sealed DT tube, for example, or alternately, neutron generator 21 may include a high-intensity plasma neutron source producing neutrons characterized by an energy of 14.4 MeV. A set of collimated energy-resolving detectors 26 are mounted in a housing 27 that can be rotated such that the detectors are able to detect gamma radiation emitted from any pre-selected point in the container lying along the neutron beam 22. Any motion of the detector housing (such as a combination of rotation and/or translation) to change the field of view of the energy-resolving detectors is within the scope of this invention. Radiation emitted from this one point only is detected, due to collimation of the path 28 defining a field of view of detectors 26. Alternatively, a fixed array of collimated energy-resolving detectors can be employed, instead of one or more detectors mounted in a rotating housing. Each detector element of the array then detects gamma radiation from separate discrete line segments along the neutron beam. The energy resolving detectors ideally have the highest possible energy resolution available. This is currently achieved using cooled high-purity germanium detectors. However, alternative, less-expensive detector materials with a lower energy resolution could also be used such as NaT scintillation crystals, or CdZnTe solid state detectors.

As the container 10 is rotated on platform 20, the system acquires x-ray transmission images of the container from many different angles. Typically, the images will be acquired at angular increments of between 1 and 5 degrees, depending on the accuracy that is required for the tomographic reconstruction. Container 10 is also gradually raised as it is rotated, with the result that x-ray images are taken at many different angles through each vertical slice of the container. For example, 360 images might be acquired at 1 degree increments for each 2-cm vertical slice of the container. As the images for each slice are acquired, the data can be reconstructed using computer algorithms known in the art. Typically this is performed using the algorithm of "filtered back-projection" (as described, for example, by Epstein, Mathematics of Medical Imaging, (Prentice Hall, 2003), which is incorporated herein by reference. Alternatively, any of a variety of tomographic analysis algorithms known in the art may be employed to obtain the reconstruction.

The CT scan produces a plurality of reconstructed slices through the container, each of which shows the cross-sectional shapes of all objects 30 contained in the slice, and their CT-number, defined above, which, for many organic materials, is approximately proportional to their density. The ensemble of slices may be referred to herein in the aggregate as a "three-dimensional image" of the enclosure that has been scanned.

The system software implemented by a first processor 124 keeps track of the location and size of all regions in the reconstructed slices which have a reconstructed CT number or density in the range of interest. It is to be understood that first processor 124 may comprise part of processor 24 and may be identical thereto. Suspect regions 30 can then be interrogated using the level-two neutron beam. This interrogation stage may be performed either immediately after each slice has been reconstructed, or alternatively, each of the suspect regions may be interrogated after the X-Ray CT scan of the entire container has been completed. This may be performed as the container is lowered again to its original starting position, in one embodiment.

The level-two material identification interrogation sequence is as follows:

1. Container 10 is raised or lowered such that suspect region 30 is positioned level with the height of the fixed neutron beam 22.

2. Container 10 is rotated such that the center of the suspect region 30 is aligned with the neutron beam 22, and positioned as close to the source 21 of the neutrons as possible.

3. The housing 27 containing the collimated energy resolving detectors is rotated and/or translated such that the field of view of the detector is directed at the center of the suspect region 30.

4. The neutron beam is activated, and inelastic scattering interactions of the high-energy neutrons with the nuclei of the atoms contained in the suspect material leaves the nuclei in excited nuclear states. When these states decay (which occurs almost instantaneously) they emit characteristic gamma rays, with the energy of the gamma rays indicating uniquely which nuclei the decay occurred in. For example, following inelastic interactions with high-energy neutrons, carbon nuclei emit gamma rays with an energy of 4.4 MeV, oxygen nuclei emit gamma rays at 6.0 MeV, and nitrogen nuclei emit gamma rays with energies of 2.8 and 5.7 MeV. It is to be understood that detection, in this manner, of other elemental compositions is within the scope of the invention as described and as claimed in any appended claims.

5. The gamma rays 32 emitted from the suspect region 30 are detected by the energy-resolving detectors 26. As soon as there are a sufficient number of detected gamma rays in the acquired energy spectrum to unambiguously identify the suspect material, the neutron beam is turned off. The system then repeats the process, and positions the next suspect region into the neutron beam for interrogation. The process continues until all suspect regions have been interrogated.

6. The energy spectrum acquired for each suspect region is analyzed, and is then compared using statistical analysis algorithms with a library of energy spectra of threat items stored in a database. If a match is found and the calculated mass of the threat material is above a predetermined threshold, an alarm is sounded. The object is then highlighted on a computer monitor for the operator to inspect in more detail. Alternatively, the number of characteristic gamma rays corresponding to carbon (C), nitrogen (N) and oxygen (O) nuclei are determined by looking at the number of counts in the respective regions of interest (ROI) of the energy spectrum. From these numbers, ratios indicative of contraband materials can be formed, For example, regions with a high nitrogen content and a relatively low carbon to oxygen ratio are indicative of explosives, whilst the presence of certain illicit drugs can be determined by calculating the carbon/oxygen and carbon/nitrogen ratios.

To aid in the resolution of any automatically generated system alarms, each of the reconstructed tomographic slice images may be presented to an operator for further visual inspection, with the suspect threat items highlighted. In addition, the tomographic slices can be combined to allow a three-dimensional model of the container to be presented to the operator. The operator also has the ability to rotate the container on the screen, and to view its contents from any angle.

Exemplary System Performance

The time it takes to scan an LD3 container in the system is limited by the maximum speed at which the container can be rotated without its contents shifting significantly. For example, if a separation between vertical slices of 5 cm is required, the total number of slices in an LD3 container is about 33. Assuming a rotation speed of 11 rpm (one rotation every 5.5 seconds), the level one CT scan requires about three minutes. If a 10 kW, 450 kV x-ray tube is employed in the system as the source 14 of x-rays, and 360 images are acquired per slice, this yields an integration time of about 15.3 ms per x-ray view. With this integration time, the total penetration of the CT system is about 6 inches of steel equivalent. For dense cargos such as pallets of frozen meat, a 4 or 6 MeV linear accelerator may be required as the source of x-rays, in order to provide sufficient penetration of the cargo.

The neutron interrogation is performed on all regions in the container which have a reconstructed density or CT number in the threat range, and which have sufficient size and mass to classify them as a threat. For example, one of the regions may be identified by the level one CT scan as an explosive with a mass of about one pound. The time needed to acquire enough characteristic gamma rays to identify the suspect material is dependent on several factors:

1. The intensity of the neutron source.
2. The distance from the neutron source to the voxel in the container containing the suspect material.
3. The number, size, energy resolution, and detection efficiency of the energy resolving detectors.
4. The distance from the detectors to the voxel containing the suspect material.
5. The attenuation of the incoming neutrons in any intervening material in the cargo.
6. The attenuation of the outgoing characteristic gamma rays in any overlying material in the cargo.

For example, if a deuterium-tritium plasma neutron source with a neutron flux of $5 \times 10^{12}$ neutrons/second is used in conjunction with three 75-mm high-purity germanium detectors, then a useful energy spectrum containing 1,000 detected gamma ray lines can be acquired in about 3 seconds (this example assumes 5 cm voxels, a source/voxel distance of 250 cm, and a detector/voxel distance of 185 cm). This means that the material in each suspect region can be identified in about 3 seconds. If it is assumed that there are twenty such regions in a container, then the neutron interrogation process will take about one minute, plus the time required to position each suspect region into the neutron beam. The total scan time of the container (CT scan plus neutron interrogation) can therefore be completed in less than about five minutes.

The present invention may be practiced in accordance with numerous alternate embodiments. Some alternate embodiments are now described:

The level one X-Ray CT system may alternatively consist of a rotating gantry that rotates around the container, allowing the container under inspection to remain fixed. In this embodiment, either the inspected enclosure or the sources are positioned so as to direct both the level two neutron beam and the field-of-view of the energy resolving detectors onto the region in the container containing the suspect material.

The source of penetrating radiation for the level one X-Ray CT scan is not limited to an x-ray tube but can also be produced from an accelerator, a linear accelerator (linac), or a radioactive source. The end-point energy of the source is not limited to any particular value, but must be sufficiently high so that the radiation penetrates each point of the container for each of the rotational views.

The level one x-ray CT scan can be performed using dual-energy CT, in order to reduce further the number of false alarms from the level-one system. This will result in a reduced number of suspect regions which need to be interrogated by the level-two system.

The level-one x-ray CT scan can be performed using a cone-beam of x-rays and a two-dimensional detector array, rather than a fan beam and a one-dimensional detector array.

A fast reconstruction can be performed on each slice of x-ray CT data as it is acquired. This would allow a second scan of the same slice to be acquired at higher statistics should there be any regions that exhibit a density in, or close to, the threat density range.

More than one neutron beam can be employed in order to increase the neutron flux incident on any suspect region being interrogated.

The energy of the neutron beam is not limited to 14 MeV, but can be varied in order to look for different excitation modes of the material under interrogation.

In accordance with an alternate embodiment of the invention, a neutron detector 35 is be placed on the other side of the container from the neutron source, allowing neutron transmission imaging to be performed simultaneously with the CT scan.

The level-two neutron interrogation may be performed either after the CT scan of the entire container has been completed, or it can be done during the CT scan after each slice has been reconstructed and any suspect regions in that slice have been identified.

All of the heretofore described embodiments of the invention are intended to be merely exemplary and numerous variations and modifications will be apparent to those skilled in the art. All such variations and modifications are intended to be within the scope of the present invention as defined in any appended claims.

What is claimed is:

1. A method for identifying materials of interest within an enclosure, the method comprising:
   a. rotating the enclosure about a first axis;
   b. obtaining a three-dimensional image indicative of at least one of a CT number and density of contents of the enclosure;
   c. identifying a suspect region of contents of the enclosure based on at least one of the CT number and density;
   d. activating a collimated neutron beam to traverse a suspect region;
   e. rotating a collimated gamma radiation detector about a second axis noncoincident with the first axis such that the detector intercepts fluorescent emission from the suspect region traversed by the collimated neutron beam;
   f. detecting fluorescent emission from the suspect region; and
   g. characterizing material within the suspect region based at least on the detected fluorescent emission.

2. A method in accordance with claim 1, wherein obtaining a three-dimensional image includes scanning the enclosure with penetrating radiation.

3. A method in accordance with claim 2, wherein scanning the enclosure with penetrating radiation includes penetrating the enclosure with x-rays.

4. A method in accordance with claim 1, wherein obtaining a three-dimensional image further includes detecting penetrating radiation after traversal of the enclosure.

5. A method in accordance with claim 1, wherein obtaining a three-dimensional image further includes energy resolution of penetrating radiation traversing the enclosure.

6. A method in accordance with claim 1, wherein the step of obtaining a three-dimensional image includes rotating the enclosure.

7. A method in accordance with claim 1, wherein the step of obtaining a three-dimensional image includes elevating the enclosure during a scan of the enclosure with penetrating radiation.

8. A method in accordance with claim 1, further including detecting neutrons from the neutron beam which traverses the enclosure.

9. A method in accordance with claim 1, wherein the step of detecting fluorescent emission from the suspect region includes resolving an energy characterizing the fluorescent emission.

10. A method in accordance with claim 1, wherein the step of detecting fluorescent emission from the suspect region includes at least one of rotating and translating a field of view of an energy-resolving detector.

11. A system for identifying materials of interest within an enclosure, the system comprising:
   a. a CT scanner for obtaining a three-dimensional image indicative of at least one of a CT number, and density of contents of the enclosure, the CT scanner including a stage for supporting the enclosure, the stage rotatable about a first axis;
   b. a first processor for identifying a suspect region of contents of the enclosure based on at least one of the CT number and density;
   c. a source for generating a collimated neutron beam to traverse the suspect region of contents of the enclosure;
   d. a rotatable detector for detecting fluorescent emission from the suspect region upon rotation of the detector about a second axis noncoincident with the first axis; and
   e. a second processor for characterizing material within the suspect region based at least on the detected fluorescent emission.

12. A system in accordance with claim 11, wherein the first and second processors are embodied in a single processor.

13. A system in accordance with claim 11, wherein the CT scanner includes a source of x-rays.

14. A system in accordance with claim 11, wherein the CT scanner includes a linear accelerator.

15. A system in accordance with claim 11, wherein the CT scanner includes an array of detector elements.

16. A system in accordance with claim 15, wherein the array of detector elements includes a linear array of detector elements.

17. A system in accordance with claim 15, wherein the array of detector elements includes a two-dimensional array of detector elements.

18. A system in accordance with claim 15, wherein the array of detector elements includes energy resolving detector elements.

19. A system in accordance with claim 11, further comprising a neutron detector disposed distally to the source for generating a collimated neutron beam with respect to the enclosure.

20. A system in accordance with claim 11, wherein the detector for detecting fluorescent emission from the suspect region includes an energy-sensitive detector.

* * * * *